(12) United States Patent
Tomlinson et al.

(10) Patent No.: US 8,680,338 B2
(45) Date of Patent: Mar. 25, 2014

(54) LOW-VOC POLYAMINO ALCOHOLS

(71) Applicants: Angus Chemical Company, Buffalo Grove, IL (US); Dow Global Technologies LLC, Midland, MI (US)

(72) Inventors: Ian A. Tomlinson, Midland, MI (US); Asghar A. Peera, Cary, IL (US)

(73) Assignee: ANGUS Chemical Company, Buffalo Grove, IL (US)

( * ) Notice: Subject to any disclaimer, the term of this patent is extended or adjusted under 35 U.S.C. 154(b) by 0 days.

(21) Appl. No.: 14/036,560

(22) Filed: Sep. 25, 2013

(65) Prior Publication Data

US 2014/0020601 A1 Jan. 23, 2014

Related U.S. Application Data

(62) Division of application No. 13/316,716, filed on Dec. 12, 2011, now Pat. No. 8,575,396.

(51) Int. Cl.
    *C07C 215/12* (2006.01)
(52) U.S. Cl.
    USPC ............................ 564/506; 564/504; 564/507
(58) Field of Classification Search
    USPC ....................................................... 564/506
    See application file for complete search history.

(56) References Cited

U.S. PATENT DOCUMENTS

| | | |
|---|---|---|
| 2,157,386 A | 5/1939 | Johnson |
| 2,347,621 A | 4/1944 | Tindall |
| 2,381,408 A | 8/1945 | Senkus et al. |
| 2,393,825 A | 1/1946 | Senkus et al. |
| 2,413,153 A | 12/1946 | O'Loughlin |
| 2,421,165 A | 5/1947 | Senkus et al. |
| 2,587,572 A | 2/1952 | Tryon |
| 2,673,880 A | 3/1954 | Eldred et al. |
| 3,054,748 A | 9/1962 | Hodge et al. |
| 4,410,746 A | 10/1983 | Eckler |
| 5,336,784 A | 8/1994 | Hiskey et al. |
| 7,445,771 B2 | 11/2008 | Dassanayake et al. |
| 2010/0275816 A1 | 11/2010 | Swedo |
| 2012/0035298 A1 | 2/2012 | Tomlinson et al. |

FOREIGN PATENT DOCUMENTS

| | | |
|---|---|---|
| EP | 0325277 A2 | 7/1989 |
| GB | 939777 A | 10/1963 |
| WO | 2005056515 A2 | 6/2005 |

OTHER PUBLICATIONS

Database Caplus on STN, Acc. No. 1946:533, Senkus, (Aug. 7, 1945) (abstract).
Database Caplus on STN, Acc. No. 1963:45995, Hodge, (Sep. 18, 1962) (abstract).
Johnson, "Reaction of Aliphatic Amines with Formaldehyde and Nitroparaffins. II. Secondary Amies", J. American Chem. Soc., vol. 68, No. 1, pp. 12-14 (1946).
Lawrance, G., et al.; "Metal-directed synthesis of the new potentially pentadentate aminoalcohol ligand 5-amino-5-methyl-3,7-diazanonane-1,9-diol based on ethanolamine." Polyhedron, vol. 7. No. 14. pp. 1263-1266. (1988).
Senkus, M., "Reaction of primary aliphatic amines with formaldehyde and nitroparaffins," J. American Chemical Society, vol. 68. pp. 10-12. (1946).

*Primary Examiner* — Brian J Davis
(74) *Attorney, Agent, or Firm* — Kenneth Crimaldi

(57) ABSTRACT

A method for adjusting pH in an aqueous coating composition having an initial pH less than 7 by adding to the aqueous coating composition a compound having formula (V)

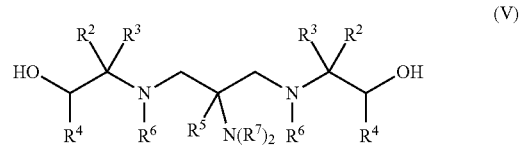

(V)

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)$ $(N(R^7)_2)CH_2OH$; and $R^7$ is hydrogen or methyl.

4 Claims, No Drawings

LOW-VOC POLYAMINO ALCOHOLS

BACKGROUND

This invention relates generally to a polyamine compound useful in coating compositions and other applications for pH adjustment.

Compounds with multiple amino and/or hydroxyl groups are known. For example, M. Senkus, *J. Am. Chem. Soc.* (1946), 68, 10-12, discloses a compound having the formula

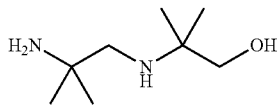

but this reference does not disclose or suggest a polyamino-polyalcohol compound as claimed in the present application.

The problem addressed by this invention is to find new low VOC polyamine compounds useful in coating compositions and other applications for pH adjustment.

STATEMENT OF INVENTION

The present invention is directed to a method for producing a polyamino-polyalcohol.

The method comprises steps of: (a) combining an aminoalcohol of formula (I)

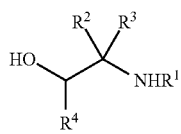

with a nitro-diol of formula (II)

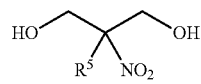

wherein $R^1$ is hydrogen, hydroxyethyl or $C_1$-$C_{10}$ alkyl; $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is methyl or ethyl; to produce a nitro amino diol; and (b) contacting said nitro amino diol with a reducing agent capable of reducing aliphatic nitro groups.

The present invention is further directed to a compound having formula (III)

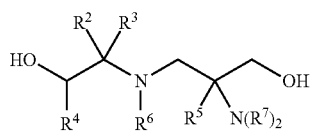

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)$ $(N(R^7)_2)CH_2OH$; and $R^7$ is hydrogen or methyl.

The present invention is further directed to a compound having formula (IV)

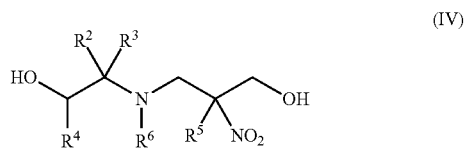

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)$ $(NO_2)CH_2OH$.

The present invention is further directed to a compound having formula (V)

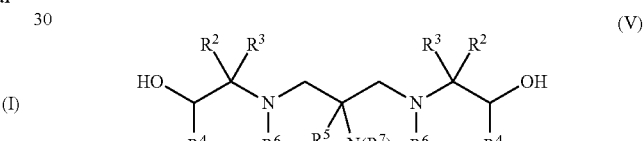

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)$ $(N(R^7)_2)CH_2OH$; and $R^7$ is hydrogen or methyl.

The present invention is further directed to a compound having formula (VI)

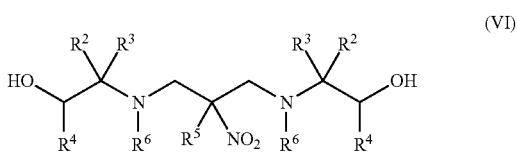

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)$ $(NO_2)CH_2OH$.

DETAILED DESCRIPTION

All percentages are weight percentages ("wt %"), unless otherwise indicated. Concentrations in parts per million ("ppm") are calculated on a weight/volume basis. An "aqueous" composition is one comprising at least 30 wt % water, preferably at least 35 wt % water, preferably at least 38 wt % water. Preferably, aqueous compositions comprise no more than 5 wt % organic solvent. An "alkyl" group is a hydrocarbyl group having from one to twenty carbon atoms, unless otherwise specified, in a linear or branched arrangement. Alkyl groups optionally have one or more double or triple bonds. Substitution on alkyl groups of one or more hydroxy or alkoxy groups is permitted. Preferably, alkyl groups are saturated and unsubstituted. A difunctional group is a substituent group having two points of attachment, e.g., one example of a difunctional alkyl group would be —$(CH_2)_x$—, where x could be from two to twenty.

In the method of this invention, preferably $R^1$ is hydrogen; $R^2$ and $R^3$ independently are hydrogen, methyl or ethyl; $R^4$ is hydrogen; and $R^5$ is hydrogen, methyl or ethyl. Preferably, $R^5$ is methyl. Preferably, $R^2$ and $R^3$ are methyl.

In the compounds of this invention, preferably $R^2$ and $R^3$ independently are hydrogen, methyl or ethyl; $R^4$ is hydrogen; $R^5$ is hydrogen, methyl or ethyl; and $R^6$ is hydrogen or —$CH_2C(R^5)(N(R^7)_2)CH_2OH$ (in compounds III and V) or —$CH_2C(R^5)(NO_2)CH_2OH$ (in compounds IV and VI). Preferably, $R^2$ and $R^3$ are methyl. Preferably, $R^4$ is hydrogen. Preferably, $R^5$ is methyl. Preferably, $R^6$ is hydrogen.

In some embodiments of the invention, $R^2$ and $R^3$ combine with a carbon to which both are attached to form a five-membered or six-membered saturated carbocyclic ring, i.e., $R^2$ and $R^3$ together represent a $C_4$-$C_5$ difunctional group having formula —$(CH_2)_4$— or —$(CH_2)_5$—. For example, in compound (I) when $R^2$ and $R^3$ represent —$(CH_2)_5$—, the structure would be

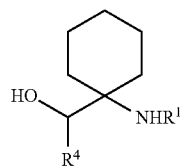

Reduction of nitro compounds (IV) and (VI) may be accomplished using any reagent capable of reducing aliphatic nitro groups. Examples of such reducing agents include hydrogen gas in combination with a catalyst, for example, Raney nickel, a platinum or palladium based catalyst (Pt or Pd in elemental form or as oxides, with or without supports e.g. carbon); and other reducing agents including metal/acid combinations, e.g. iron/acetic acid; and aluminum hydrides, e.g., VITRIDE. Preferred reducing agents include hydrogen gas in combination with any of the following catalysts: Raney nickel, Platinum or palladium. Conditions for hydrogenation of nitro groups are well known, e.g., a temperature range of about 20-80° C. at a pressure of about 100-1000 psi (690-6900 kPa) and these can be adjusted easily by one skilled in the art. Reduction of these compounds in the presence of excess formaldehyde and temperature between 60-140° C., reduces the aliphatic nitro groups to dimethylamino groups instead of amino groups, corresponding to $R^7$=methyl in compounds (III) and (V). Preferably, formaldehyde is present in 100-200% of the stoichiometric amount required to fully methylate the amines present in the reduced compound. Reduction without formaldehyde will produce compounds having $R^7$=hydrogen.

Preferably, compound (VI) is prepared using a molar ratio of compound (I) to compound (II) of approximately two:one, resulting in one mole of compound (I) becoming attached to each end of compound (II). Preferably, the molar ratio of (I) to (II) is from 2.3:1 to 1.5:1, preferably from 2.1:1 to 1.8:1. However, if the ratio of compound (I) to compound (II) is approximately one:two, then compound (IV) in which $R^6$ is $CH_2C(NO_2)(R^1)(CH_2OH)$ will be formed. In this case, clearly $R^1$ in compound (I) must be hydrogen. Preferably, if compound (IV) in which $R^6$ is $CH_2C(NO_2)(R^1)(CH_2OH)$ is desired, the molar ratio of (I) to (II) is from 1:1.5 to 1:2.3, preferably from 1:1.8 to 1:2.1. Preferably, if compound (IV) in which $R^6$ is hydrogen, hydroxyethyl or $C_1$-$C_{10}$ alkyl is desired, then the molar ratio of compound (I) to compound (II) is approximately one:one. Preferably, the molar ratio of (I) to (II) is from 1.2:1 to 0.8:1, preferably from 1.1:1 to 0.9:1.

When the compound of formula (III) or (V) is used to adjust pH in an aqueous coating composition or other aqueous composition having an initial pH less than 7, the amount of compound added clearly can vary depending on the initial pH, desired final pH, and other components present in the composition. However, one skilled in the art can easily determine the necessary amount of these compounds to be added. In acrylic latex coating compositions, typically the amount would be in the range from 10 wt % to 125 wt % of total weight of carboxylic acid groups in the coating composition, alternatively from 25 wt % to 100 wt %. In some embodiments of the invention, the initial pH of the aqueous composition is from 2-7, alternatively from 2.5-6. The target pH value preferably is from 7.8 to 9.5, alternatively from 8 to 9.2. In some embodiments of the invention, the aqueous coating composition is an acrylic latex comprising copolymers of acrylic or methacrylic acid with $C_1$-$C_8$ alkyl acrylates or methacrylates. In some embodiments of the invention, the acrylic latex comprises 40-65 wt % polymer solids, alternatively 45-62 wt %, alternatively 45-55 wt %.

Conditions for reaction of compounds (1) and (II) are generally known, e.g., typically the reactants are heated to reflux for 1-14 hours and then optionally kept at room temperature (20-25° C.) for up to 24-48 hours. There are many suitable solvents, e.g., water, methanol, ethanol, and mixtures thereof.

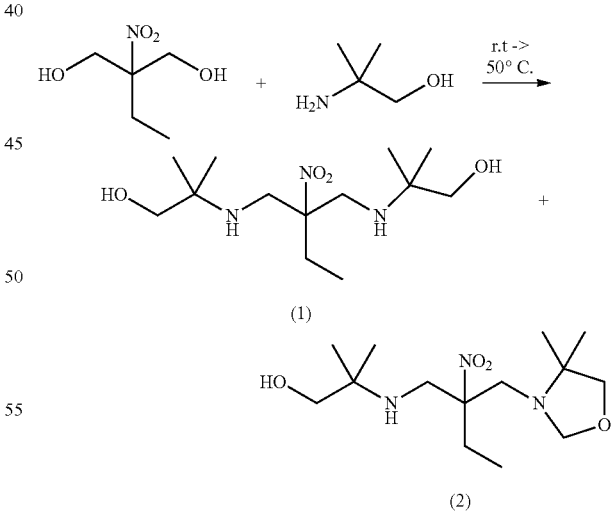

A 500 mL 3-neck flask equipped with a magnetic stirrer, nitrogen blanket, thermocouple controlled heating mantle and addition funnel is charged with 2-ethyl-2-nitropropane-1,3-diol (69.2 wt % NEPD in water: 72.3 g/0.336 moles, 1 equivalent). The addition funnel is charged with 2-amino-2-methylpropan-1-ol, AMP-95 (89% AMP: 67.2 g/0.671 moles, 2 equivalents). The AMP added to the NEPD solution over a period of 30 minutes, while stirring under a nitrogen blanket. A mild exotherm is noted at the beginning of the addition. The reaction was stirred overnight at room temperature, followed by heating the reaction mixture to 50° C. for additional 8-10 hrs. The yellow solution turned brown upon heating. LC/MS analysis of the reaction showed a mixture of two compounds. The major product was compound (2) i.e., 2-(2-((4,4-dimethyloxazolidin-3-yl)methyl)-2-nitrobutylamino)-2-methylpropan-1-ol, [M+H]=304.22 and the minor product was compound (I) with [M+H]=292.22. The reaction mixture was taken as-is and hydrogenated added over a period of 30 minutes while maintaining the reactor at 60° C./600 psi hydrogen. When the addition is completed, the autoclave temperature is increased to 100° C. and temperature maintained for 30 minutes. Followed by temperature increase to 110° C. for additional 30 minutes; finally, the temperature ramped up to 120° C. and reaction mixture in the autoclave stirred for 90 minutes at that temperature to ensure complete opening of the oxazolidine ring. At this point, the reaction deemed complete. After cooling to room temperature, the reactor is vented, opened and the crude

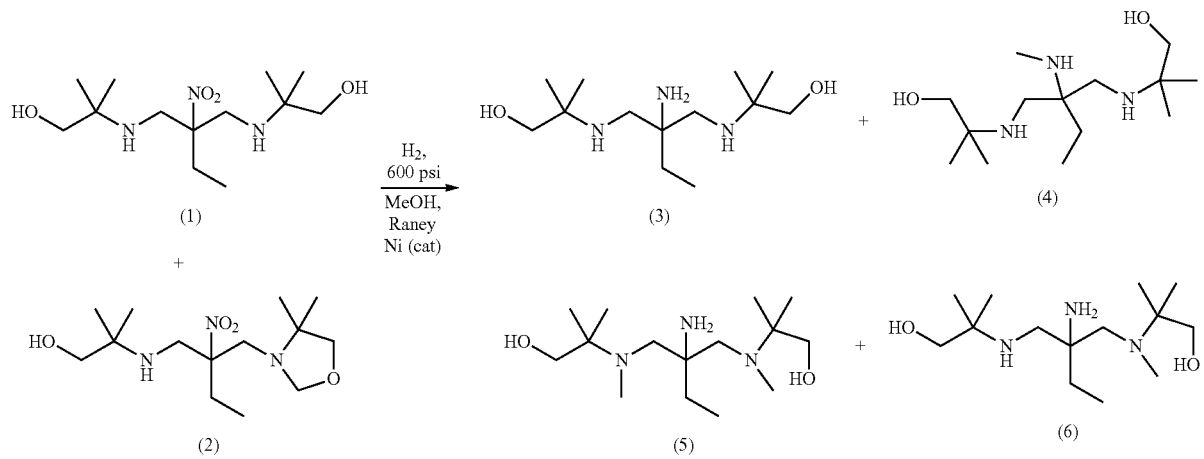

A 2-liter Parr autoclave is charged with methanol (300 mL) and Raney Nickel catalyst (R-3111, 16.3 g wet weight). The reactor is sealed, purged with nitrogen followed by purging with hydrogen and then brought up to 60° C. under 426 psi hydrogen pressure. When the temperature reaches the desired mark, the reactor pressure increased to approximately 600 psi. With rapid stirring (600-640 rpm), the reaction mixture from above-diluted with an additional 50 mL of methanol and product isolated via vacuum filtration. The brown filtrate is stripped on a rotary evaporator (50-55° C./29-30" vacuum) to remove water/methanol. The process resulted in approximately 16.68 g of viscous brown product. GC-MS characterized the products as a mixture of four poly-amino alcohols. Compound (3), [M+H]=262; Compound (4), [M+H]=276; Compound (5), [M+H]=290 and Compound (6), [M+H]=276.

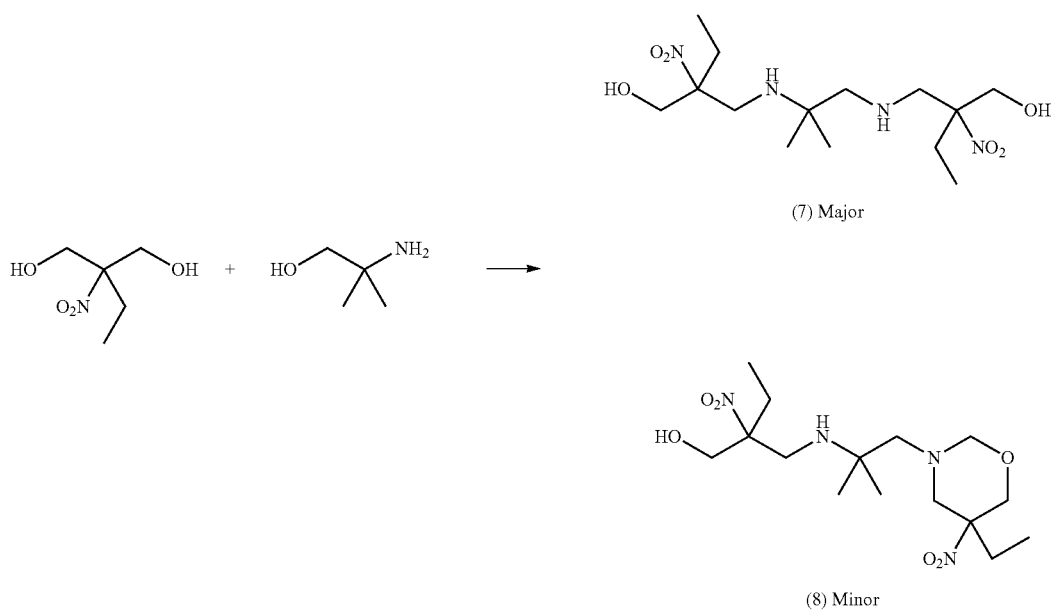

A 250 mL 1-neck flask equipped with a magnetic stirrer, nitrogen blanket and addition funnel is charged with 2-ethyl-2-nitropropane-1,3-diol (69.2 wt % NEPD in water: 73.4 g/0.341 moles, 2 equivalent). The addition funnel charged with 2-methylpropane-1,2-diamine, MDP (15 g/0.170 moles, 1 equivalent). The MDP added slowly to the NEPD solution, while stirring under a nitrogen blanket. Upon addition of MDP, the clear yellow solution turned murky. Stirring the reaction mixture overnight, resulted in two layers i.e., the aqueous layer and a gel like layer. The aqueous layer was decanted and ~59 g of gel like yellow material obtained. The LC-MS analysis showed the desired product i.e., compound (7), [M+H]=351.22 and compound (8) the oxazine, [M+H]=362.22 as the major products. The mono addition product also detected. The reaction mixture was taken as-is and hydrogenated.

release water. The source could be from excess formaldehyde in aqueous NEPD or reversal of the nitro amino alcohol.

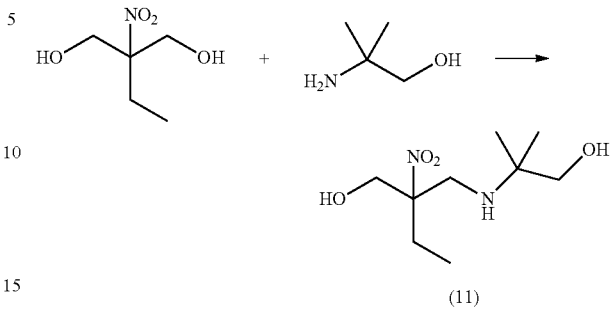

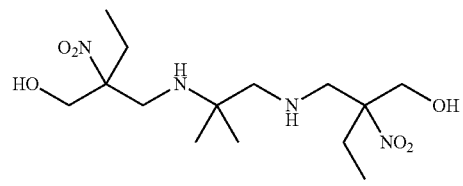

(7) Major

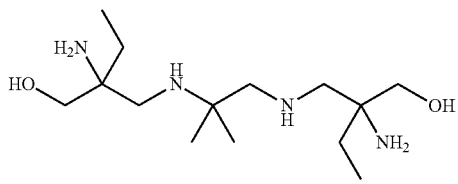

(9) Major

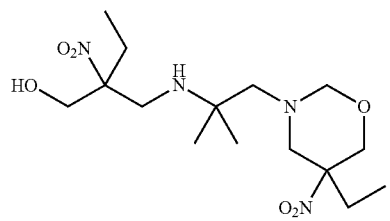

(8) Minor

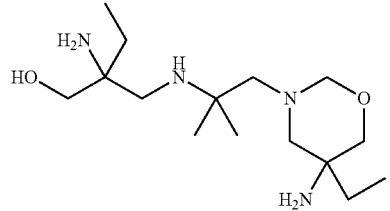

(10) Minor

A 2-liter Parr autoclave charged with methanol (300 mL) and Raney Nickel catalyst (R-3111, 12 g wet weight). The reactor is sealed, purged with nitrogen followed by purging with hydrogen and then brought up to 60° C. under 600 psi hydrogen pressure. With rapid stirring (600-620 rpm), the reaction mixture from above diluted with an additional 100 mL of methanol and added over a period of 30-45 minutes while maintaining the reactor at 60° C./600 psi hydrogen. The reaction deemed complete, when the hydrogen uptake by the reaction stopped. After cooling to room temperature, the reactor vented, opened and the crude product isolated via vacuum filtration. The yellow filtrate is stripped on a rotary evaporator (50-60° C./29-30" vacuum) to remove water/methanol. The process resulted in 34.6 g of slightly viscous product. LC-MS characterized the products as a mixture of Compound (9), [M+H]=291.27 and Compound (10), [M+H]=303.27. The major product was the poly amino oxazine, compound (10). There is formation if six member ring during hydrogenation. The ring forms when amine reacts with formaldehyde by A 100 mL 1-neck flask equipped with a magnetic stirrer, nitrogen blanket and addition funnel is charged with 2-ethyl-2-nitropropane-1,3-diol (69.2 wt % NEPD in water: 36.2 g/0.167 moles, 1 equivalent). The addition funnel charged with 2-amino-2-methylpropan-1-ol, AMP-95 (89% AMP: 8.35 g/0.084 moles, 0.5 equivalents). The AMP added to the NEPD solution over a period of 10 minutes, while stirring under a nitrogen blanket. A mild exotherm noted at the beginning of the addition. The reaction let to stir for 24 hrs at room temperature. The clear yellow solution turned opaque and milky upon stirring for 24 hrs. LC-MS analysis showed that the desired product i.e., 2-((1-hydroxy-2-methylpropan-2-ylamino)methyl)-2-nitrobutan-1-ol, compound (11) was the major product with [M+H]=221.14 and small amount of 2-(2-((4,4-dimethyloxazolidin-3-yl)methyl)-2-nitrobutylamino)-2-methylpropan-1-ol, [M+H]=304.22. There were few low boiler impurities detected also and will be removed after hydrogenation reaction. The reaction mixture was taken as-is and hydrogenated.

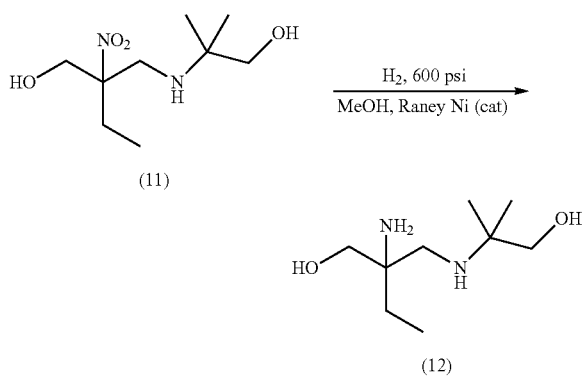

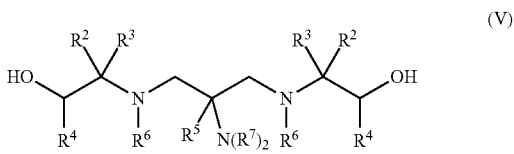

A 300 mL Parr autoclave charged with methanol (100 mL) and Raney Nickel catalyst (R-3111, 11.4 g wet weight). The reactor is sealed, purged with nitrogen followed by purging with hydrogen and then brought up to 60° C. under 700-740 psi hydrogen pressure. With rapid stirring (600-620 rpm), the orange reaction mixture from above diluted with an additional 100 mL of methanol and added over a period of 30-45 minutes while maintaining the reactor at 60° C./700 psi hydrogen. After 45 min of stirring at 60° C., the autoclave temperature increased to 70° C./735 psi, and stirred under hydrogen pressure for another 30 minutes. The temperature of the autoclave was further increased to 90° C./761 psi and the reaction mixture stirred for an additional 45 minutes. The reaction deemed complete, when the hydrogen uptake by the reaction stopped. After cooling to room temperature, the reactor vented, opened and the crude product isolated via vacuum filtration. The yellow filtrate is stripped on a rotary evaporator (50-60° C./29-30" vacuum) to remove water/methanol. The process resulted in 10.6 g of yellow viscous product. CI GC/MS characterized the products as Compound (12), 2-amino-2-((1-hydroxy-2-methylpropan-2-ylamino)methyl) butan-1-ol, with retention time of 17.7 min and [M+H]=191 as the major component. There was a peak for AEPD as a result of using excess NEPD during the Mannich reaction (example 5). The other minor impurities were the methylated amino alcohol products.

The invention claimed is:

1. A method for adjusting pH in an aqueous coating composition having an initial pH less than 7; said method comprising adding to said aqueous coating composition a compound having formula (V)

$$\text{(V)}$$

$$HO\underset{R^4}{\overset{R^2\ R^3}{\diagdown}}\underset{R^6}{\overset{}{N}}\diagdown\underset{R^5\ \ N(R^7)_2}{\overset{R^3\ R^2}{\diagdown}}\underset{R^6}{\overset{}{N}}\diagdown\underset{R^4}{\overset{}{\diagdown}}OH$$

wherein $R^2$ and $R^3$ independently are hydrogen, methyl, ethyl, hydroxymethyl, or $R^2$ and $R^3$ combine with a carbon to which they are attached to form a five-membered or six-membered saturated carbocyclic ring; $R^4$ is hydrogen or $C_1$-$C_4$ alkyl; $R^5$ is hydrogen, methyl, ethyl or hydroxymethyl; $R^6$ is hydrogen, hydroxyethyl, $C_1$-$C_{10}$ alkyl or —$CH_2C(R^5)(N(R^7)_2)CH_2OH$; and $R^7$ is hydrogen or methyl.

2. The method of claim 1 in which $R^2$ and $R^3$ independently are methyl or ethyl; $R^4$ is hydrogen; $R^5$ is methyl or ethyl; and $R^6$ is hydrogen or —$CH_2C(R^5)(NH_2)CH_2OH$.

3. The method of claim 2 in which the amount of compound (V) is in the range from 10 wt % to 125 wt % of total weight of carboxylic acid groups in the coating composition.

4. The method of claim 2 in which the compound of formula (V) is added to the aqueous coating composition in an amount sufficient to raise pH of the aqueous coating composition to a range from 7.8 to 9.5.

* * * * *